US00PP16511P3

(12) United States Plant Patent
Kaagman

(10) Patent No.: US PP16,511 P3
(45) Date of Patent: May 9, 2006

(54) ***OSTEOSPERMUM* PLANT NAMED 'OSTE DEEPPUR'**

(50) Latin Name: *Osteospermum ecklonis*
Varietal Denomination: Oste Deeppur

(75) Inventor: Pim Kaagman, Andijk (NL)

(73) Assignee: Goldsmith Seeds, Inc., Gilroy, CA (US)

( * ) Notice: Subject to any disclaimer, the term of this patent is extended or adjusted under 35 U.S.C. 154(b) by 201 days.

(21) Appl. No.: 10/885,566

(22) Filed: Jul. 6, 2004

(65) Prior Publication Data

US 2006/0010548 P1 Jan. 12, 2006

(51) Int. Cl.
*A01H 5/00* (2006.01)

(52) U.S. Cl. ..... Plt./360

(58) Field of Classification Search ..... Plt./360
See application file for complete search history.

(56) References Cited

PUBLICATIONS

The New Royal Horticultural Society Dictionary of Gardening, 1992. 1, A to C, pp. xxxv and xiii.*

* cited by examiner

*Primary Examiner*—Anne Marie Grunberg
*Assistant Examiner*—June Hwu
(74) *Attorney, Agent, or Firm*—Jondle & Associates, P.C.

(57) ABSTRACT

An *Osteospermum* cultivar particularly distinguished by purple colored flowers, dark green foliage and vigorous growth is described.

1 Drawing Sheet

Genus and species: *Osteospermum ecklonis.*
Variety denomination: 'Oste Deeppur'.

BACKGROUND OF THE NEW PLANT

The variety 'Oste Deeppur' originated from a cross made in October, 2000. The female parent is a violet proprietary line OX-51 (unpatented). The male parent is 'Denebola', (patent status unknown) which is a commercial variety. Seed from this cross was sown in June 2001. In October 2001, single-plant selections were made for vegetative propagation using plant habit and flower color as selection criteria. One selection became the new variety 'Oste Deeppur'.

'Oste Deeppur' is a product of a planned breeding program intended to create new *Osteospermum* cultivars with purple colored flowers, dark green foliage, and vigorous growth.

The new cultivar was created in 2000 in Gilroy, Calif. and has been asexually reproduced repeatedly by vegetative cuttings and tissue culture in Gilroy, Calif., and Andijk, The Netherlands over a two ½ year period. The plant has also been trialed at Gilroy, Calif., and Andijk, The Netherlands. The present invention has been found to retain its distinctive characteristics through successive propagation, and this novelty is firmly fixed.

DESCRIPTION OF PHOTOGRAPH

This new *Osteospermum* plant is illustrated by the accompanying photograph which shows blooms, buds, and foliage of the plant in full color, the colors shown being as true as can be reasonably obtained by conventional photographic procedures. Photos were taken from plants grown in The Netherlands in the late winter/spring in a greenhouse. Plants are 4½ months old, had one terminal pinch at 3 weeks old, and are grown in a 4 inch pot with 3 treatments of cyocel.

The photograph shows the mature plant with an inset photo of a close-up of the inflorescence.

DESCRIPTION OF THE NEW CULTIVAR

The following detailed descriptions set forth the distinctive characteristics of 'Oste Deeppur'. The data, which defines these characteristics, were collected from asexual reproductions carried out in Gilroy, Calif. The plant history was taken on 5½ month old plants grown in six inch pots in the early summer season, in a LEXAN covered greenhouse under natural light and color readings were taken in the greenhouse under natural lights. Color references are primarily to The R.H.S. Colour Chart of The Royal Horticultural Society of London (R.H.S.) 2001. Texture description details were observed under a dissecting microscope according to The New Royal Horticultural Society Dictionary of Gardening (1992).

THE PLANT

Classification: *Osteospermum ecklonis.*
Botanical: *Osteospermum.*
Commercial: 'Oste Deeppur'.
Form: Upright, semi-compact and mounded.
Growth and branching habit: Good vigorous, freely branched habit.
Height: From soil level to top of blooms: Approximately 40–45 cm.
Width: Approximately 45–50 cm.
Time to produce a finished flowering plant: 8–11 weeks for a 6 inch pot.
Outdoor plant performance: Herbaceous, frost tender perennial patio planters, mixed container plantings or garden beds.

Time to initiate and develop roots: Approximately 8–14 days in the greenhouse.
Root description: Fibrous, well-branched, white.

THE LEAVES

Leaf arrangement: Alternate.
Fully expanded, Length: 5.0–5.2 cm; Width: 2.8–3.0 cm.
Leaf shape: Obovate.
Leaf margin: Dentate.
Apex aspect: Broadly acute.
Base aspect: Acuminate.
Leaf color: Upper surface — RHS 147A (green); Under surface RHS 137A (green).
Leaf texture: Pilose.
Venation: Pinnate.
Venation color: RHS 144B (yellow-green).
Petiole length: 1.0 cm.
Petiole diameter: 0.4–0.5 cm.
Petiole color: RHS 144B (yellow-green).
Petiole texture: Pilose.

THE STEM

Length: 30–40 cm.
Diameter: 0.3–0.4 cm.
Stem internode length: 1.0–2.0 cm.
Color: RHS 144C (yellow-green).
Texture: Pilose.
Stem anthocyanin: None.
Peduncle color: RHS 144B (yellow-green).
Peduncle length: 6.5–12.0 cm.
Peduncle diameter: 0.2 cm.
Peduncle texture: Pilose.
Peduncle strength: Moderate to strong.

THE BUD

Shape: Ovate.
Diameter: 1.6–1.9 cm.
Length: 1.5–2.4 cm.
Color at tight bud (starting to show color): RHS 79A (purple).

THE FLOWER

Blooming habit: Plants flower freely from the spring through fall given the proper growing conditions.
Inflorescence/floret type: Terminal and axillary inflorescences held above the foliage. Capitulum inflorescence, radially symmetrical.
Flower diameter: 6.5–7.0 cm.
Average disc diameter: 1.1 cm.
Ray floret:
*Immature color.*—Upper surface is RHS N78A (purple) with longitudinal stripes of RHS 77A (purple). Some petals have irregular white margins. Under surface is RHS N77B (purple) with longitudinal stripes of RHS N77A (purple).
*Mature color.*—Upper surface is RHS N78A (purple) but with a little more red and longitudinal stripes of RHS 77A (purple). Mature under surface is same as immature under surface.
*Floret length.*—2.8–3.0 cm.
*Floret width.*—1.8–1.9 cm.
*Floret apex shape.*—Emarginate to Retuse.
*Floret base shape.*—Cuneate.
*Floret margin.*—Entire.
*Floret texture.*—Papillose on the upper surface; hirsute on the basal portion of lower surface.
*Floret quantity.*—Approximately 14.
Disc floret:
*Tube color.*—RHS N77B (purple).
*Shape.*—Tubular, elongated.
*Length.*—0.7 cm.
*Diameter at apex.*—0.2 cm.
*Apex shape.*—5-pointed, acute.
*Apex color.*—RHS N77A (purple).
*Floret quantity.*—Approximately 50.
Phyllaries:
*Color.*—RHS 144A (yellow-green).
*Length.*—0.8–0.9 cm.
*Width.*—0.15–0.2 cm.
*Shape.*—Linear.
*Apex.*—Acute.
*Texture.*—Pilose and glandular hairs.
*Longevity of individual blooms.*—7–14 days.
*Fragrance.*—None.

THE REPRODUCTIVE ORGANS

Androecium:
*Pollen color.*—RHS 13A (yellow).
*Filament color.*—RHS N155D (white).
*Length of stamen.*—0.3–0.5 cm.
*Location of androecium.*—Disc florets only.
Gynoecium:
*Pistil.*—1 per floret.
*Pistil length.*—0.5 cm.
*Stigma color.*—RHS N77A (purple).
*Style color.*—RHS N77A (purple).
*Location of gynoecium.*—Both disc florets and ray florets.
*Fruit seed set.*—Has not been observed.

DISEASE AND INSECT RESISTANCE

Has not been observed.

COMPARISON WITH KNOWN CULTIVARS

'Oste Deeppur' differs from the female parent, OX-51 in the following ways: 'Oste Deeppur' has a deeper purple color and is a later flowering plant with more vigor than OX-51.

'Oste Deeppur' differs from the male parent, 'Denebola' in the following ways: 'Oste Deeppur' has a lighter flower color, is earlier to flower, and has better branching and shorter peduncles than 'Denebola'.

'Oste Deeppur' differs from the commercial *Osteospermum* variety 'Sunny Dark Martha' in the following ways: 'Oste Deeppur' is more compact, has more branches and more flowers, has smaller leaves and is earlier to flower than 'Sunny Dark Martha.'

I claim:

1. A new and distinct cultivar of *Osteospermum* plant as shown and described herein.

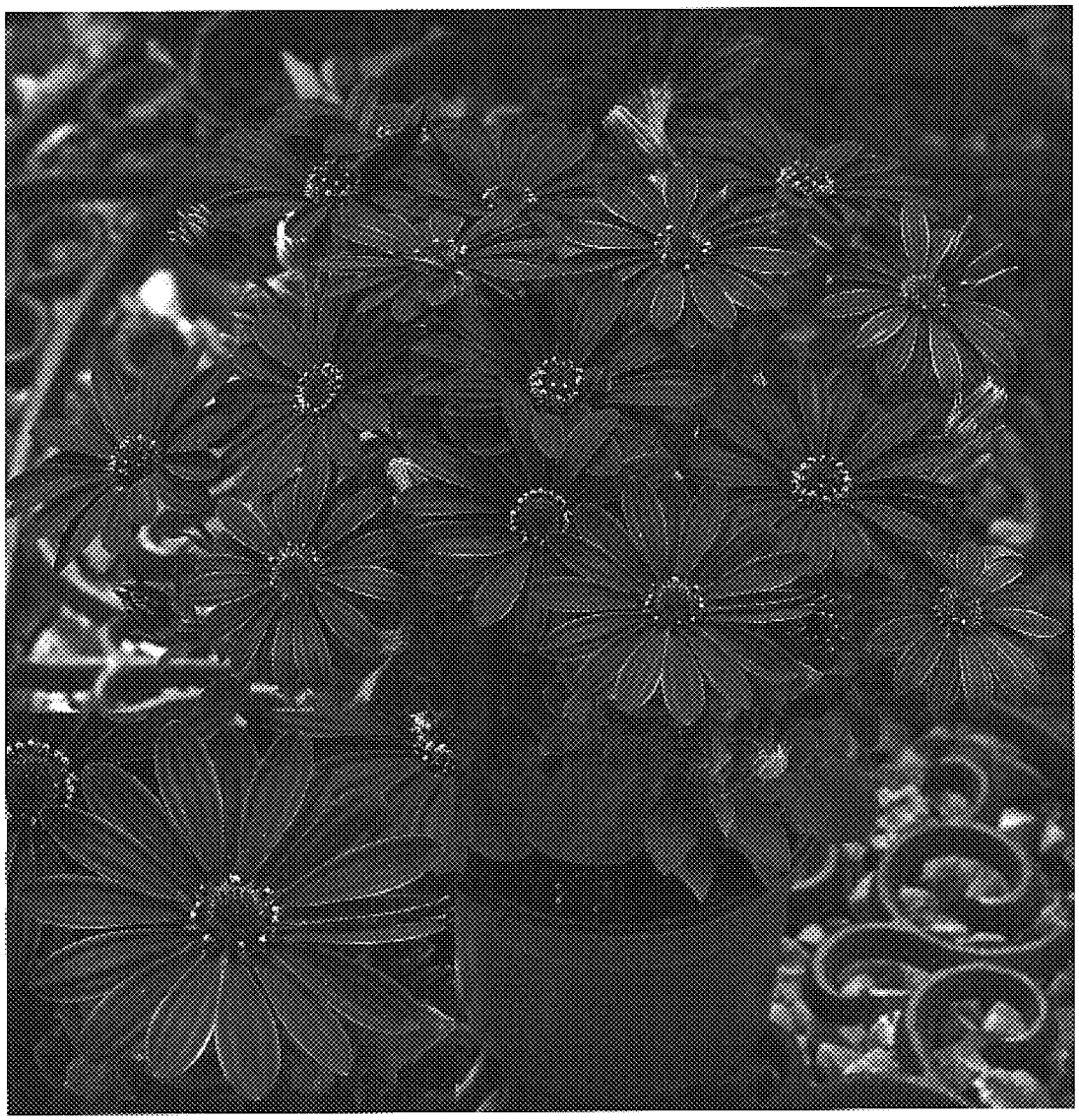

* * * * *